United States Patent [19]

Gammer

[11] Patent Number: 4,846,843
[45] Date of Patent: Jul. 11, 1989

[54] INNER HAND

[75] Inventor: Peter Gammer, Vienna, Austria

[73] Assignee: Otto Bock Orthopaedische Industrie Besitz- und Verwaltungs-Kommanditgesellschaft, Duderstadt, Fed. Rep. of Germany

[21] Appl. No.: 162,887

[22] Filed: Mar. 2, 1988

[30] Foreign Application Priority Data

Mar. 3, 1987 [DE] Fed. Rep. of Germany ....... 3706800

[51] Int. Cl.$^4$ ............................................... A61F 2/66
[52] U.S. Cl. .................................................... 623/57
[58] Field of Search .......................... 294/119, 3, 19.1; 2/163, 167, 168, 161 A, 161 R, 159, 2.21; 623/60, 61–65, 57

[56] References Cited

U.S. PATENT DOCUMENTS

| 1,055,838 | 3/1913 | Torrance | 2/161 R |
|---|---|---|---|
| 3,343,864 | 9/1967 | Baer | 294/119.3 |
| 4,038,787 | 8/1977 | Bianchi | 2/161 R |
| 4,521,924 | 6/1985 | Jacobsen et al. | 3/1.1 |
| 4,570,269 | 2/1986 | Berlese | 2/161 A |

FOREIGN PATENT DOCUMENTS 2012589 8/1979 United Kingdom .

Primary Examiner—Richard J. Apley
Assistant Examiner—James Prizant
Attorney, Agent, or Firm—Foley & Lardner, Schwartz, Jeffrey, Schwaab, Mack, Blumenthal & Evans

[57] ABSTRACT

An inner hand as an orthopedic fitting part of thermoplastic for accommodating a hand mechanism is disclosed. The inner hand has an annular groove which is made on the end portion of the hand and into which a ring which fixes the inner hand on the hand mechanism is inserted. To improve the functioning of the inner hand, a two-component sandwich design is proposed, the utilization region of at least the thumb and index finger being harder than the remaining hand element.

16 Claims, 2 Drawing Sheets

INNER HAND

BACKGROUND OF THE INVENTION

The present invention relates to an inner hand as an orthopedic fitting part, made of a thermoplastic, for accommodating a hand mechanism, having an annular groove which is made in the end portion of the hand and into which a ring which fixes the inner hand on the hand mechanism is inserted.

A prior art inner hand is produced from PVC, has a uniformly continuous wall thickness of the same material hardness and serves to cover and give shape to the hand mechanism. The annular groove is designed as a round groove in which a beaded ring is inserted.

The shape and proportion are responsible for material stresses, which arise in particular in the intermediate region between the thumb and the index finger as well as in the back part of the hand. It is this which is the cause of uneconomical energy consumption in connection with a reduced opening width between the thumb and the index finger. Only low mechanical strength is obtained at the utilization points of the thumb, index finger and middle finger and in the intermediate region between the thumb and the index finger. However, the material specific dimensional stability leads to cyclic volume displacements, especially in the end portion of the hand so that it is impossible to guarantee effective protection of the mechanism against sweat and other kinds of contamination. The homogeneous, intrinsically firm and inflexible PVC material results in relatively poor efficiency with the disadvantages mentioned above, which despite this fact have hitherto been accepted as a justifiable compromise.

SUMMARY OF THE INVENTION

It is therefore an object of the present invention to improve the functioning of an inner hand of the type described at the outset.

It is another object of the invention to provide an inner hand which combines improved mechanical wear resistance with flexibility.

It is a further object of the invention to protect a hand mechanism against sweat and other contamination.

These and other objects of the invention are achieved by providing an inner hand as an orthopedic fitting part for accommodating a hand mechanism comprising a hand element having a utilization region of at least the thumb and index finger and an end portion at least one annular groove on the end portion and a ring insertable in the annular groove for fixing the inner hand on the hand mechanism, wherein the utilization region is harder than the remainder of the hand element.

In this arrangement, it is advantageous if the utilization region is composed of compact plastic while the remaining hand element is composed of closed-cell foamed plastic. This produces a two-component sandwich design which may also be referred to as a hybrid design. Thus, the inner hand according to the invention exhibits a sharp distinction between the two regions, the Shore hardness of the utilization region being about 80 and that of the remainder of the hand element being about 50. The inner hand according to the invention thus comprises two materials of different degrees of hardness and physical properties.

In conjunction with the flexibly foamed PVC, a new shape and proportion results in a stress-free, energy saving and complete opening between the thumb and the index finger. The harder-formulation material in the utilization region increases the mechanical wear resistance and serves to prevent cold flow in these zones.

To improve the opening range between the thumb and the index finger even more while ensuring a high degree of wear resistance, it is advantageous if ribbed-shaped material reinforcements ("ribs") are provided in the region of the hand element between the thumb and the index finger. At the same time, it is advantageous if the wall thickness of the hand element between the ribs is less than in the remaining region of the hand element and if the ribs extend approximately parallel to one another and in each case lie in planes which extend perpendicular to the plane defined by the thumb and index finger.

The surface of the ribs forms a wear-resistant zone between the thumb and index finger, the reduced wall thickness between the ribs guaranteeing adequate flexibility. In addition, the arrangement of the ribs makes it possible for the ribs to lean against one another in the manner of radii, resulting in low force material deformation when the thumb and index finger are brought together To protect the mechanism more effectively against sweat and other kinds of contamination, it is possible to provide the end portion of the hand with two grooves into which annular webs of a ring, which fits around the end portion of the hand in the region of the two annular grooves, fit. In this arrangement, it is advantageous if the outer annular groove is made deeper than the inner annular groove and the annular web allocated to the outer annular groove is correspondingly broader than the other annular web.

The axial and radial forces determined by the internal diameter of the ring and by the arrangement of the annular webs produce optimum contact pressure on the hand mechanism chassis to be sealed. At the same time, an improvement in the mechanical securing of the inner hand on the hand mechanism results.

Further features of the invention are the subject of the subclaims and are explained in greater detail in conjunction with further advantages of the invention with reference to an exemplary embodiment.

BRIEF DESCRIPTION OF THE DRAWINGS

An exemplary embodiment of the invention is illustrated in the drawing, in which.

DETAILED DESCRIPTION OF THE PREFERRED EMBODIMENTS

Figure 1:
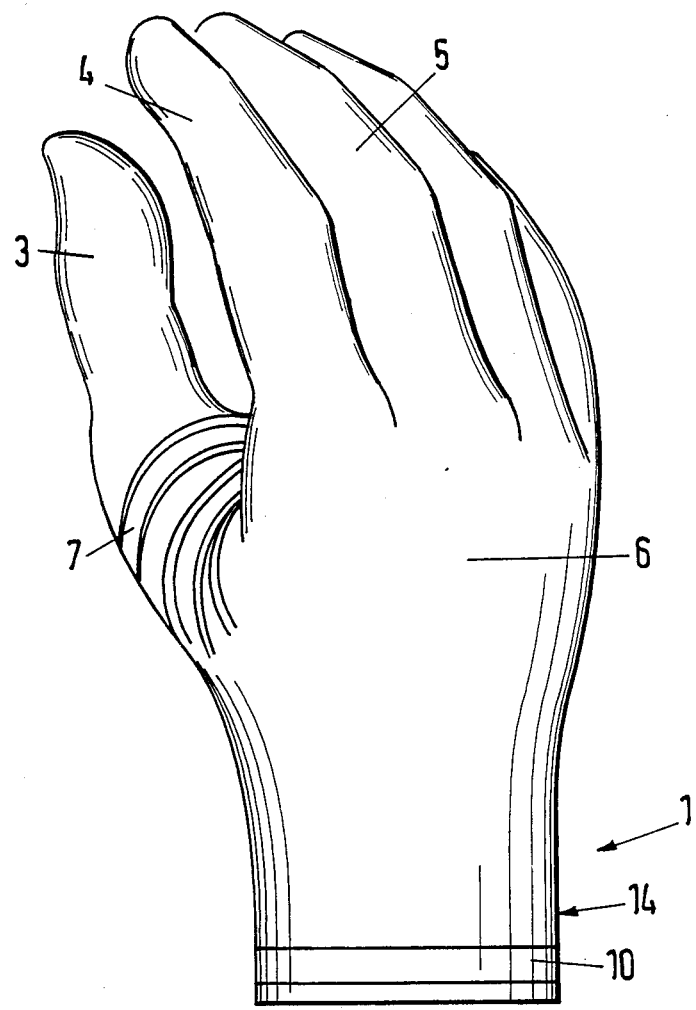
FIG. 1 shows an inner hand, represented diagrammatically.

The inner hand is an orthopedic fitting part, made of a thermoplastic, for accommodating a hand mechanism. The finger and knuckle regions are designed with attention to cosmetic detail. When this inner hand is used by the wearer of the prosthesis, the inner hand is usually concealed by a cosmetic glove. At the end portion 1 of the hand, the inner hand is attached to a hand mechanism (not shown in greater detail), which protrudes into the inner hand and controls the movement of at least the thumb and index finger.

According to the invention, the inner hand is composed of a combination of two materials having different degrees of hardness and physical properties. In this hand, the utilization region 2 of the thumb 3 as well as that of the index finger 4 and of the middle finger 5 is composed of a firm, compact thermoplastic, preferably PVC, having a Shore hardness of about 80. The remaining hand element 6 immediately adjoining this utilization region 2 is composed of a softer material having a bubble structure and is designed as a closed-cell foamed plastic having a Shore hardness of about 50. It is therefore what is referred to as a two-component sandwich design or a hybrid design.

Figure 2:
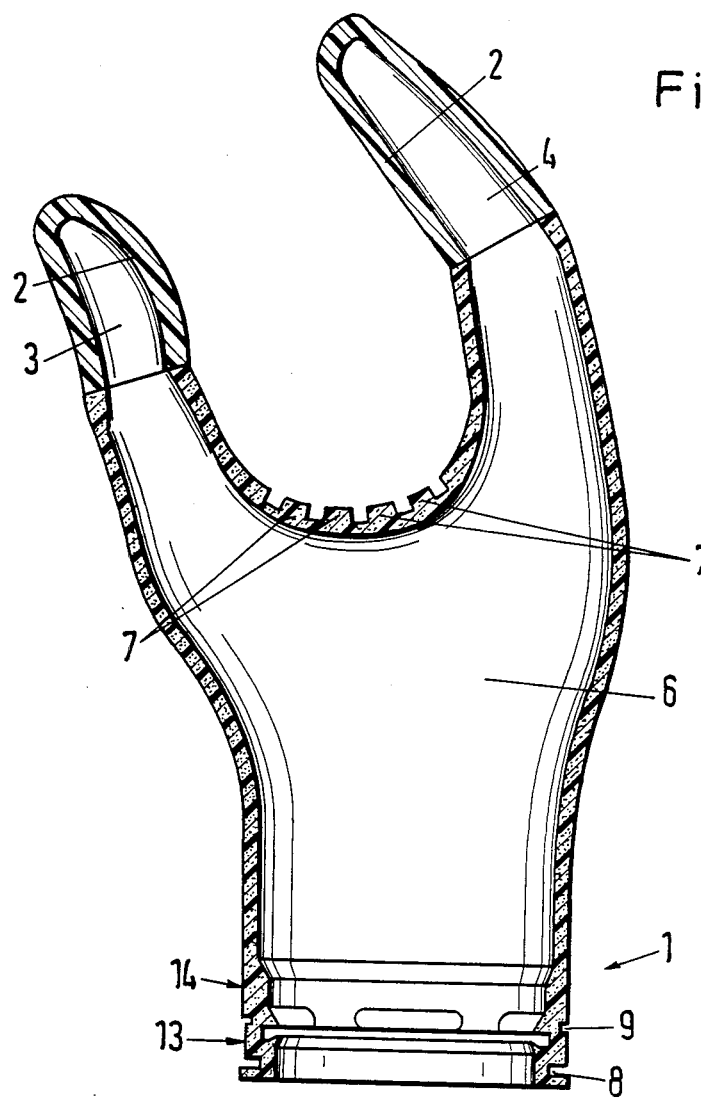
FIG. 2 shows a longitudinal section in the plane formed by the thumb and index finger.

Rib-shaped material reinforcements, referred to as ribs 7, are provided in the region of the hand element between the thumb 3 and the index finger 4. These ribs 7 extend approximately parallel to one another and in each case lie in planes which extend perpendicular to the plane defined by the thumb 3 and the index finger 4, this being the plane in which FIG. 2 is drawn. As can be seen from FIG. 2, the wall thickness of the hand element 6 between the ribs 7 is less than in the remaining region of the hand element.

The hard-formulation utilization region 2 and the rib-shaped material reinforcement between the thumb and index finger are stabilizing measures against mechanical wear. The arrangement and design of the ribs 7 is selected such that when the thumb 3 and index finger 4 are brought together, the ribs 7 can lean against one another in the manner of radii, thereby ensuring low-force material deformation.

Figure 3:
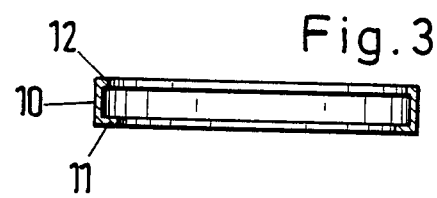
FIG. 3 shows a cross-section through a ring.

Two annular grooves 8,9, the outer annular groove 8 of which is made deeper than the inner annular grove 9, are provided in the end portion 1 of the hand. A ring 10, which fits into the annular grooves 8,9 by annular webs 11,12, fits over the two annular grooves 8,9, the annular web 11 allocated to the outer annular groove 8 being correspondingly broader than the other annular web 12. An annular recessed portion 13 which accommodates the ring 10 is made in the surface of the end portion 1 of the hand with the result that the ring 10 lies virtually flush in the surface 14 of the end portion 1 of the hand. This can be seen in FIG. 1 while, in FIG. 2, for the sake of greater clarity, ring 10 has been omitted. The design of the ring is shown in FIG. 3.

What is claimed is:

1. An inner hand as an orthopedic fitting part for accommodating and covering a prosthetic hand mechanism, comprising:
    a hand element, comprising a utilization region consisting essentially of at least a portion of digits, said digits including at least a thumb and an index finger;
    at least one annular groove on an end portion; and
    a ring insertable in the annular groove for fixing the inner hand on the hand mechanism;
    wherein the utilization region and the remainder of the hand element substantially entirely formed of plastic and the utilization region is formed of plastic which is harder than the plastic which forms the remainder of the hand element.

2. An inner hand as claimed in claim 1, wherein the utilization region comprises compact plastic and the remainder of the hand element comprises closed-cell foamed plastic.

3. An inner hand as claimed in claim 1, wherein the Shore hardness of the utilization region is about 80 and that of the remainder of the hand element is about 50.

4. An inner hand as claimed in claim 1, additionally comprising ribs in the region of the hand element between the thumb and the index finger.

5. An inner hand as claimed in claim 4, wherein the wall thickness of the hand element between the ribs is less than in the remainder of the hand element.

6. An inner hand as claimed in claim 4, wherein the ribs extend approximately parallel to one another and in each case lie in planes which extend perpendicular to the plane defined by the thumb and index finger.

7. An inner hand as claimed in claim 1, wherein the end portion of the hand is provided with two grooves into which annular webs of the ring fit.

8. An inner hand as claimed in claim 7, wherein a first one of the annular grooves is made deeper than a second one of the annular grooves and the annular web corresponding to the first annular groove is correspondingly broader than the second annular web.

9. An inner hand as claimed in claim 7, further comprising an annular recessed portion between the first and second annular grooves so that the ring lies virtually flush in the surface of the end portion of the hand element.

10. An inner hand as claimed in claim 2, wherein the Shore hardness of the utilization region is about 80 and that of the remainder of the hand element is about 50.

11. An inner hand as claimed in claim 3, additionally comprising ribs in the region of the hand element between the thumb and the index finger.

12. An inner hand as claimed in claim 5, wherein the ribs extend approximately parallel to one another and in each case lie in planes which extend perpendicular to the plane defined by the thumb and index finger.

13. An inner hand as claimed in claim 12, wherein the end portion of the hand is provided with two grooves into which annular webs of the ring fit.

14. An inner hand as claimed in claim 8, further comprising an annular recessed portion between the first and second annular grooves so that the ring lies virtually flush in the surface of the end portion of the hand element.

15. An inner hand as claimed in claim 11, wherein the wall thickness of the hand element between the ribs is less than in the remainder of the hand element.

16. An inner hand as claimed in claim 15, wherein the end portion of the hand is provided with two grooves into which annular webs of the ring fit.

* * * * *